United States Patent [19]

O'Sullivan

[11] Patent Number: 5,572,757
[45] Date of Patent: Nov. 12, 1996

[54] BODY SUPPORT HAVING HINGEDLY CONNECTED SEMI-CYLINDRICAL CUSHIONS

[76] Inventor: Dennis C. O'Sullivan, 774 Mays Blvd., #10, Incline Village, Nev. 89451

[21] Appl. No.: 399,964

[22] Filed: Mar. 6, 1995

[51] Int. Cl.$^6$ .................................................. A47G 9/00
[52] U.S. Cl. ........................ 5/636; 5/632; 5/640; 5/911; 297/284.5
[58] Field of Search ................................ 5/632, 636, 640, 5/630, 644, 911, 421; 297/284.5; D6/601

[56] References Cited

U.S. PATENT DOCUMENTS

| | | |
|---|---|---|
| D. 47,140 | 3/1915 | Newkirk . |
| D. 251,985 | 5/1979 | Martin .................................. D24/64 |
| D. 259,689 | 6/1981 | Handel ................................. D6/200 |
| D. 282,427 | 2/1986 | O'Sullivan ........................... D6/601 |
| D. 295,936 | 5/1988 | Sanders ................................ D6/601 |
| D. 298,198 | 10/1988 | O'Sullivan ........................... D6/601 |
| D. 307,526 | 5/1990 | McIntyre et al. ..................... D6/601 |
| D. 307,752 | 5/1990 | Yoshida et al. ...................... D14/240 |
| D. 316,451 | 4/1991 | Carnathan et al. ................... D6/601 |
| D. 330,989 | 11/1992 | Evans ................................... D6/601 |
| D. 341,509 | 11/1993 | Evans ................................... D6/601 |
| 1,549,601 | 8/1925 | Mulgrew . |
| 2,013,481 | 9/1935 | Stonehill .............................. D6/601 |
| 2,765,480 | 10/1956 | Mueller ................................ 5/640 |
| 2,877,472 | 3/1959 | Wagner ................................ D6/601 |
| 2,952,856 | 9/1960 | Ruff ..................................... 5/640 |
| 3,143,748 | 8/1964 | Manning .............................. 5/344 |
| 3,243,828 | 4/1966 | McCarty .............................. 5/338 |
| 3,261,035 | 7/1966 | Slocum ................................ 5/338 |
| 3,268,922 | 8/1966 | Moxley ................................ 5/344 |
| 3,279,849 | 10/1966 | Radke et al. ......................... 297/284 |
| 3,299,451 | 1/1967 | Trogdon ............................... 5/337 |
| 3,308,490 | 3/1967 | Cacioppo ............................. 5/345 |
| 3,542,421 | 11/1970 | Ambrose .............................. 297/230 |
| 3,638,251 | 2/1972 | Weiss ................................... 5/334 C |
| 3,849,810 | 11/1974 | Degen .................................. 5/341 |
| 3,968,529 | 7/1976 | Levin et al. .......................... 5/338 |
| 4,017,118 | 4/1977 | Cawley ................................ 297/284 |
| 4,097,087 | 6/1978 | Garavaglia .......................... 297/284 |
| 4,210,244 | 7/1980 | Westrick .............................. 206/373 |
| 4,231,125 | 11/1980 | Tittl ...................................... 5/419 |
| 4,309,784 | 1/1982 | Cohen .................................. 5/442 |
| 4,394,783 | 7/1983 | Simmons ............................. 5/432 |
| 4,413,368 | 11/1983 | Schuetze ............................. 5/494 |
| 4,506,396 | 3/1985 | Ritchie, Jr. et al. ................. 5/431 |
| 4,513,462 | 4/1985 | Thomas ............................... 5/442 |
| 4,655,502 | 4/1987 | Houllis ................................ 297/229 |

(List continued on next page.)

FOREIGN PATENT DOCUMENTS

| | | |
|---|---|---|
| 0302426A1 | 7/1988 | European Pat. Off. ............. 5/645 |
| 1127948 | 12/1956 | France . |
| 3138463A1 | 4/1983 | Germany . |
| 16809 | of 1908 | United Kingdom ................ 5/490 |
| 26072 | of 1909 | United Kingdom ................ 5/437 |
| 1837 | of 1912 | United Kingdom . |
| 1590583 | 6/1981 | United Kingdom . |

*Primary Examiner*—Alexander Grosz
*Attorney, Agent, or Firm*—Limbach & Limbach L.L.P.

[57] ABSTRACT

A body support includes first and second resilient cushions. The first cushion has a substantially semicylindrical shape defined by a semicylindrical top surface, two substantially semicircular end surfaces, and a substantially rectangular bottom surface having first and second long sides and two short sides. The second cushion has a substantially semicylindrical shape defined by a semicylindrical top surface, two substantially semicircular end surfaces, and a substantially rectangular bottom surface having first and second long sides and two short sides. The first long side of the second cushion is hingedly connected to the second long side of the first cushion so that the first and second cushions can be rotated with respect to each other from an open position to a closed position. A zipper is used to secure the first and second cushions in the closed position. A method of providing support to a person's neck and head, and a method of providing support to a person's back are also disclosed. A body support comprised of three semicylindrically shaped cushions is also disclosed.

6 Claims, 6 Drawing Sheets

U.S. PATENT DOCUMENTS

| | | | |
|---|---|---|---|
| 4,666,207 | 5/1987 | Quartano | 297/229 |
| 4,679,848 | 7/1987 | Spierings | 297/284 |
| 4,682,691 | 7/1987 | Spiering | 206/373 |
| 4,688,286 | 8/1987 | Miker, Jr. | 5/490 |
| 4,754,513 | 7/1988 | Rinz | 5/490 |
| 4,761,011 | 8/1988 | Sereboff | 297/230 |
| 4,770,466 | 9/1988 | Pesterfield | 297/391 |
| 4,777,678 | 10/1988 | Moore | 5/431 |
| 4,783,866 | 11/1988 | Simmons et al. | 5/441 |
| 4,794,657 | 1/1989 | Avery | 5/431 |
| 4,843,662 | 7/1989 | Handelman | 5/420 |
| 4,853,994 | 8/1989 | Ekstein | 5/437 |
| 4,862,536 | 9/1989 | Pruit | 5/432 |
| 4,864,668 | 9/1989 | Crisp | 5/432 |
| 4,876,755 | 10/1989 | Parrish | 5/431 |
| 4,908,894 | 3/1990 | Sanders | 5/436 |
| 4,941,222 | 7/1990 | Prager | 5/111 |
| 4,945,589 | 8/1990 | Carey | 5/442 |
| 4,949,411 | 8/1990 | Tesch | 5/434 |
| 5,015,036 | 5/1991 | Fergie | 297/397 |
| 5,088,141 | 2/1992 | Meyer et al. | 5/464 |
| 5,168,590 | 12/1992 | O'Sullivan | 5/490 |
| 5,297,304 | 3/1994 | O'Sullivan | 5/630 |
| 5,367,731 | 11/1994 | O'Sullivan | 5/645 |

BODY SUPPORT HAVING HINGEDLY CONNECTED SEMI-CYLINDRICAL CUSHIONS

BACKGROUND OF THE INVENTION

1. Field of the Invention

The present invention relates to body supports, and more particularly, to a body support having hingedly connected semicylindrical cushions.

2. Description of the Related Art

Orthopedic pillows and pillow cases have been developed to provide support to a person's neck and/or lower back. U.S. Pat. No. 4,876,755 to Parrish, for example, discloses a support cushion device including two or three cushion devices of a semi-cylindrical shape with Velcro strips positioned to allow the cushions to be fastened together to form a cylindrical shape, a "T" shape, or an "H" shape. However, when the Parrish device is used as a neck support it does not have a configuration which can simultaneously provide support to the rear portion of the head. This results in the entire weight of the person's head and neck being supported at the neck alone which can cause a strain on the neck rather than a comfortable therapeutic effect. Similarly, when the Parrish device is used as a lumbar support it does not have a configuration which can simultaneously provide support to the lumbar region and the region just below the lumbar region, which can cause a strain on the lumbar rather than a comfortable therapeutic effect.

U.S. Pat. No. 3,299,451 to Trogdon discloses a convertible pillow which may be changed from a conventional shape, i.e., a comparatively flat member having a rectangular cross section, to a generally cylindrical shape. A zipper is used to secure the pillow in the cylindrical shape. The Trogdon pillow suffers from the disadvantage that when it is in the open, unzipped position, it is simply a conventionally shaped flat pillow that provides no support or therapeutic effect to the neck. Furthermore, because the Trogdon pillow is a conventionally shaped flat pillow, it is believed that when it is converted to a generally cylindrical shape, it will be a rather large, fat configuration that will force a person's head up too high. Such a configuration can induce a strain on the neck and actually have a detrimental effect. Similar to the Parrish device, the Trogdon pillow also does not have a configuration in which support is given both to the back of the head and to the neck. Trogdon does not state that his pillow has any therapeutic effect. Instead, Trogdon states that the pillow can be used to prevent pressure from being applied to a woman's hair curlers.

Other conventional support devices suffer from a number of disadvantages. For example, many conventional support devices have predetermined shapes, thicknesses, and firmnesses that cannot be adjusted. Because people have many different shapes and sizes, most of the conventional devices cannot be used by everyone. Furthermore, although the predetermined shape, thickness, and firmness of a conventional device may be adequate for a person under some circumstances, it may not be appropriate for that person under all circumstances, such as during more severe or minor cases of fatigue.

Therefore, there is a need for a body support device that overcomes the disadvantages and limitations of conventional support devices.

SUMMARY OF THE INVENTION

The present invention provides a body support which includes a first cushion and a second cushion. The first cushion has a substantially semicylindrical shape defined by a semicylindrical top surface, two substantially semicircular end surfaces, and a substantially rectangular bottom surface having first and second long sides and two short sides. The second cushion has a substantially semicylindrical shape defined by a semicylindrical top surface, two substantially semicircular end surfaces, and a substantially rectangular bottom surface having first and second long sides and two short sides. The first long side of the second cushion is positioned substantially parallel to and hingedly connected to the second long side of the first cushion so that the first and second cushions can be rotated with respect to each other.

The present invention also provides a method of providing support to a person's neck and head. The method includes the steps of: positioning a substantially semicylindrical shaped first cushion in contact with a back portion of the neck so that a semicylindrical top surface thereof is positioned in contact with the neck; and positioning a substantially semicylindrical shaped second cushion in contact with a back portion of the head so that a semicylindrical top surface thereof is positioned in contact with the head. A first long side of the second cushion is positioned substantially parallel to and hingedly connected to a second long side of the first cushion so that the second cushion does not move away from the first cushion.

The present invention also provides a method of providing support to a person's back. The method includes the steps of: positioning a substantially semicylindrical shaped first cushion in contact with a lumbar region of the back so that a semicylindrical top surface thereof is positioned in contact with the lumbar region of the back; and positioning a substantially semicylindrical shaped second cushion in contact with a second region of the back so that a semicylindrical top surface thereof is positioned in contact with the second region of the back. A first long side of the second cushion being positioned substantially parallel to and hingedly connected to a second long side of the first cushion so that the second cushion does not move away from the first cushion.

A better understanding of the features and advantages of the present invention will be obtained by reference to the following detailed description of the invention and accompanying drawings which set forth an illustrative embodiment in which the principles of the invention are utilized.

DETAILED DESCRIPTION OF THE PREFERRED EMBODIMENTS

Figure 1:
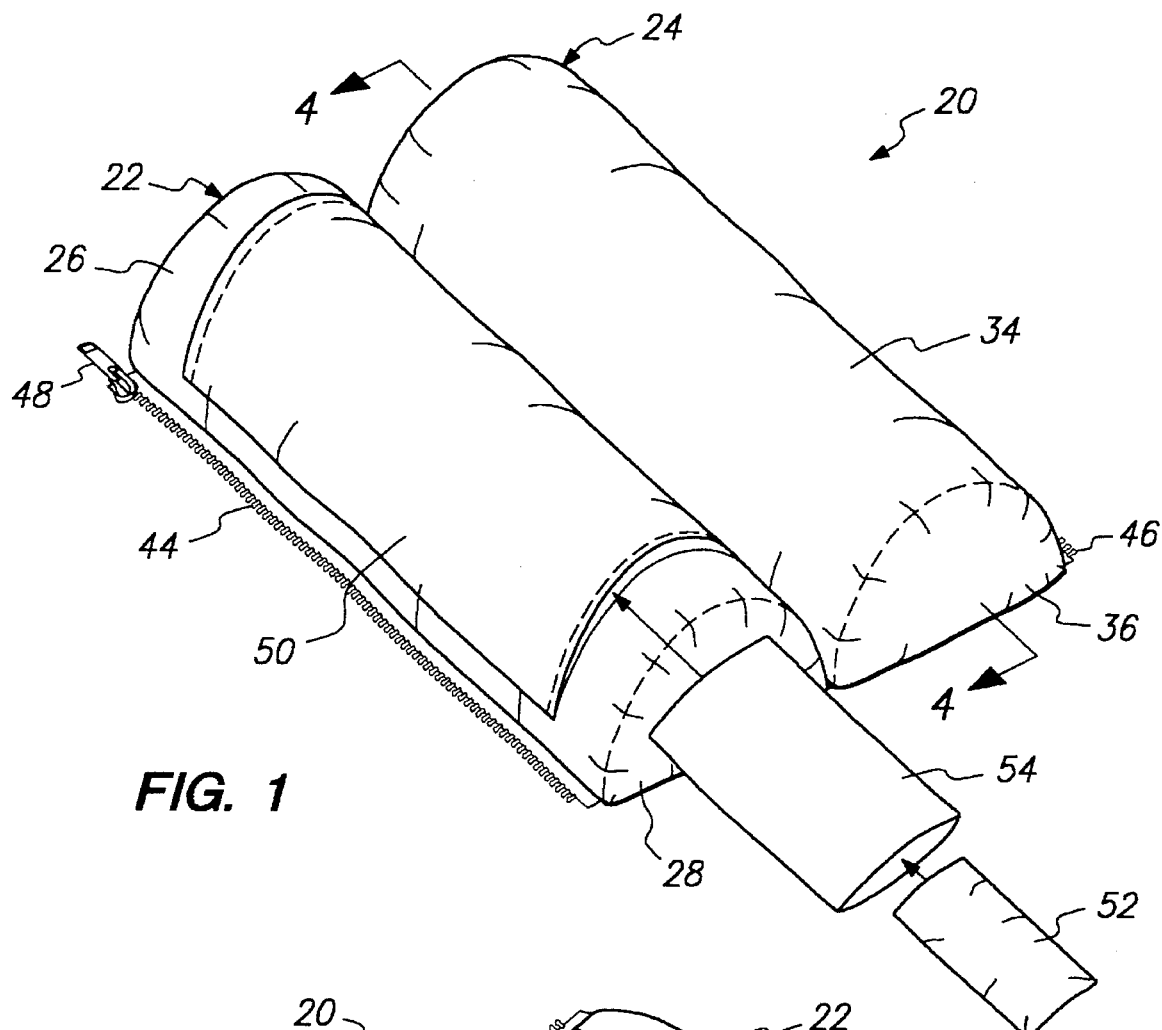
FIG. 1 is a perspective view which illustrates one embodiment of a body support in accordance with the present invention.
Figure 2:
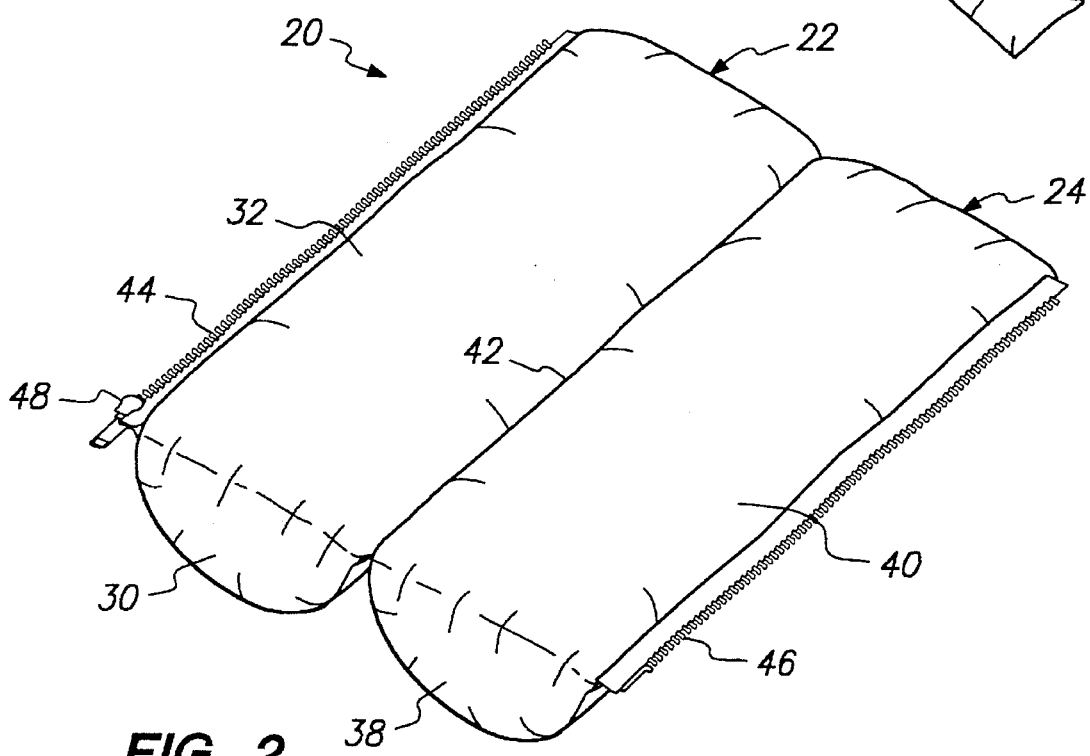
FIG. 2 is a perspective view which illustrates the bottom side of the body support shown in FIG. 1.

FIGS. 1 and 2 illustrate one embodiment of a double cushion body support 20 in accordance with the present invention. The double cushion body support 20 includes two substantially semicylindrical shaped cushions 22 and 24 which are hingedly connected together. The cushion 22 is defined by a semicylindrical top surface 26, two substantially semicircular end surfaces 28 and 30, and a substantially rectangular bottom surface 32. The bottom surface 32 has two long sides and two short sides. Similarly, the cushion 24 is defined by a semicylindrical top surface 34, two substantially semicircular end surfaces 36 and 38, and a substantially rectangular bottom surface 40. The bottom surface 40 also has two long sides and two short sides.

The cushions 22 and 24 are substantially the same size, i.e., they have the same diameter and length. However, as will be discussed below, another embodiment of the present invention utilizes semicylindrical cushions having different diameters. Furthermore, it is envisioned that the cushions of a body support in accordance with the present invention could have different lengths.

With respect to the specific diameter of the cushions 22 and 24, it should be well understood that the diameter may be adjusted without departing from the scope of the present invention. However, it has been found that a diameter of approximately 6 inches, i.e., a radius of 3 inches, provides particularly good support.

Although virtually any type of material may be used to form the outer cloth covering of the cushions 22 and 24, it has been found that poly cotton or polar fleece works particularly well. Furthermore, the cushions 22 and 24 are preferably stuffed with a material which makes them resilient, such as polyester fiber. However, it should be well understood that the cushions 22 and 24 may be stuffed with other types of stuffing, such as feathers, down, foam rubber, polyurethane foam, and the like.

The quantity of polyester fiber, or other stuffing, that is contained in the cushions 22 and 24 is preferably an amount such that the bottom surfaces 32 and 40 are slightly convex in shape. In other words, the bottom surfaces 32 and 40 tend to bulge outward. As will be discussed below, such a shape provides comfortable support when the cushions 22 and 24 are in the open position and provides a firm neck roll when the cushions are in the closed position. However, the convex shape of the bottom surfaces 32 and 40 is not required.

The cushions 22 and 24 are hingedly connected together at the connection seam 42. Specifically, one long side of the bottom surface 32 of the cushion 22 is positioned substantially parallel to one long side of the bottom surface 40 of the cushion 24. The two long sides are then hingedly connected together so that the cushions 22 and 24 can be rotated with respect to each other. Preferably, the hinged connection is made at the connection seam 42 by using one continuous piece of material for the top surfaces 26 and 34 of the cushions 22 and 24, respectively, and one continuous piece of material for the bottom surfaces 32 and 40 of the cushions 22 and 24, respectively. The material used for the top surfaces 26 and 34 is then stitched directly to the material used for the bottom surfaces 32 and 40 along the connection seam 42.

Figure 3:
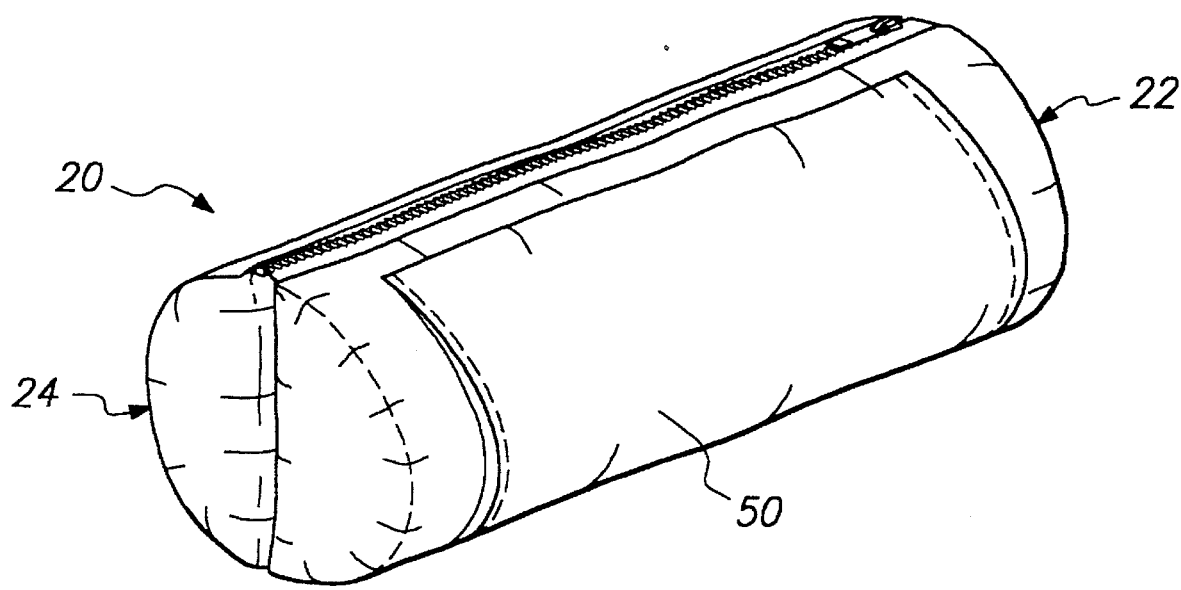
FIG. 3 is a perspective view which illustrates the body support shown in FIG. 1 in the closed position.

The hinged connection along the connection seam 42 allows the cushions 22 and 24 to be rotated from an open position to a closed position. In the open position, which is shown in FIGS. 1 and 2, the long sides of the bottom surfaces 32 and 40 opposite the connection seam 42 are positioned a maximum distance apart. FIG. 3 illustrates the cushions 22 and 24 in the closed position. In the closed position the bottom surfaces 32 and 40 are brought into contact with each other so that the cushions 22 and 24 form a substantially cylindrical configuration. Because the bottom surfaces 32 and 40 are convex in shape, the cross-section of the double cushion body support 20 may actually be slightly oval in shape.

The cushions 22 and 24 tend to spring apart from the closed position to the open position due to the bottom surfaces 32 and 40 being convex in shape. Thus, the cushions 22 and 24 usually have to be squeezed together in order to hold them in the closed position. Preferably, a zipper having zipper sections 44 and 46 is used to secure the cushions 22 and 24 in the closed position. The zipper section 44 is attached to the bottom surface 32 along the long side that is opposite the connection seam 42, and the zipper section 46 is attached to the bottom surface 40 along the long side that is opposite the connection seam 42. The zipper sections 44 and 46 are zipped together to secure the cushions 22 and 24 in the closed position. Zipping the zipper sections 44 and 46 together creates a firm neck roll due in part to the slightly convex shape of the bottom surfaces 32 and 40.

Preferably, the zipper handle 48 is made of a soft material such as leather or nylon; however, this is certainly not a requirement and a metal or hard plastic handle is sufficient. Although the zipper 44, 46 is the preferred means for securing the cushions 22 and 24 in the closed position, it should be well understood that other means, such as snaps, buttons, VELCRO brand hook and loop fabric fastening means, and the like, may also be used to secure the cushions 22 and 24 in the closed position in accordance with the present invention.

A sleeve (or pocket) 50 may be attached to one or both of the top surfaces 26 or 34 of the cushions 22 or 24, respectively. The sleeve is preferably a single piece of material that is sewed directed to the top surface 26 (or the top surface 34). The purpose of the sleeve 50 is to receive and secure a hot or cold pack 52. It is generally understood that a hot pack will soothe sore, tense muscles, and that a cold pack will help relive pain and inflammation. It is recommended that a terrycloth protector 54 be placed around the hot/cold pack 52 before it is inserted into the sleeve 50 in order to absorb condensation. Alternatively, the inside of the sleeve may be lined with the terrycloth protector 54. It should be well understood that the sleeve 50, hot/cold pack 52, and terrycloth protector 54 are all optional features of the present invention.

Figure 4:
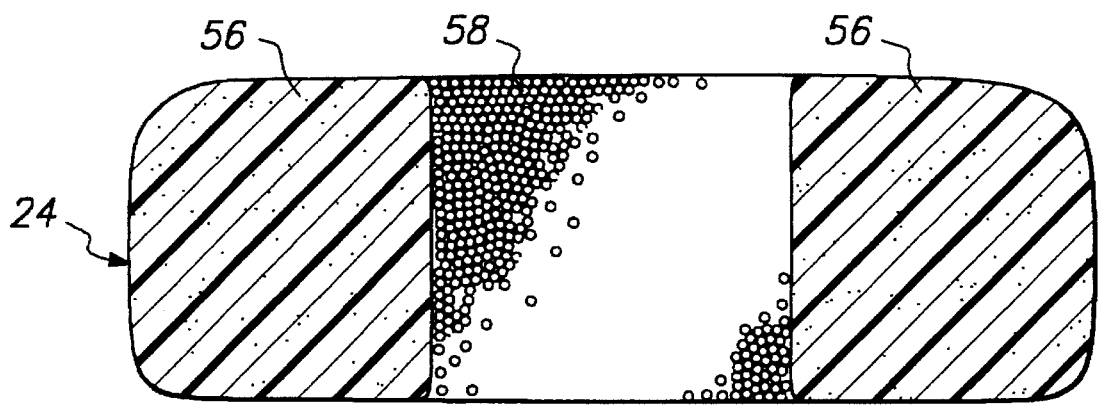
FIG. 4 is a cross-sectional view taken along line 4—4 in FIG. 1.

As mentioned above, the cushions 22 and 24 may be stuffed solely with polyester fiber, or some other type of stuffing. Alternatively, one or both of the cushions 22 or 24 may be stuffed with two or more different types of stuffing. As shown in FIG. 4, a portion of the cushion 24 may be filled with bead-like objects 58. Specifically, the cushion 24 may be divided into three sections and stuffed with polyester fiber 56 in the end sections and with bead-like objects 58 in the middle section. The bead-like objects 58 may be, for example, small round or oval balls made out of plastic or wood, dried beans, or the like, and having diameters anywhere from 6 mm to 15 mm, although they could be larger or smaller, and different size beads may be mixed together. The bead-like objects 58 give a different type of therapeutic effect than the polyester fiber 56 which some people find more comfortable; for example, the bead-like objects 58 can improve air circulation through the cushion. In addition, the bead-like objects 58 are preferably wrapped in an elastic material, such as a portion of a nylon stocking, before they are inserted into the cushion 24. It should be well understood that the use of the bead-like objects 58 in one or both of the cushions 22 or 24 is an optional feature of the present invention.

Figure 5:
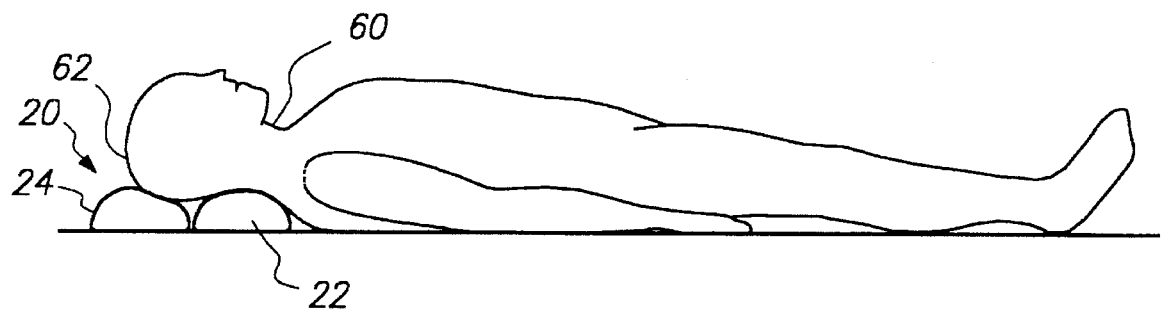
FIGS. 5–8 are side views which illustrate several uses of the body support shown in FIG. 1.

Referring to FIG. 5, the double cushion body support 20 can be used in the open, unzipped position to provide moderate support to a person's neck 60. Specifically, the cushion 22, which may or may not have the optional sleeve 50 attached thereto, is positioned under the neck 60. Once the cushion 22 is placed under the neck 60, the other cushion 24 provides support to the back of the person's head 62. Because the cushion 24 provides support to the back of the person's head 62, the support given to the person's neck 60 by the cushion 22 is not so firm that a strain is placed on the neck 60 as with the conventional neck supports discussed above. Instead, the support provided to the neck 60 is a very comfortable, moderate support. Furthermore, because the cushion 24 is attached to the cushion 22 along the connection seam 42, the cushion 24 will be secured in position under the head 62 and will not slide away from the head 62.

Figure 6:
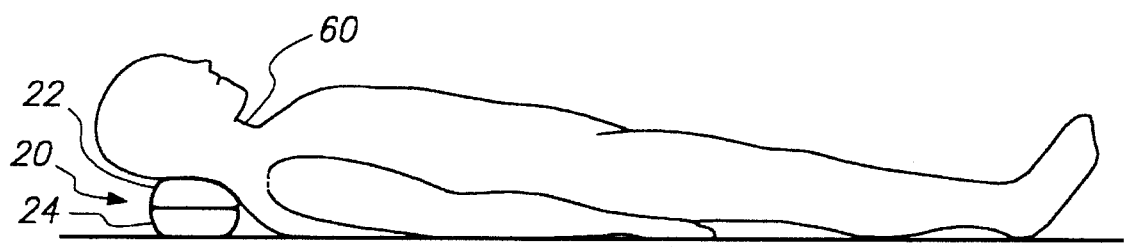

Sometimes more support is needed under the person's neck 60 and no support is needed under the head 62. In this scenario, the double cushion body support 20 can be used in the closed, zipped position as shown in FIG. 6. When used in this manner, the body support 20 provides maximum support to the person's neck 60. In both the open and closed positions, a hot or cold pack can be inserted in the sleeve 50 (if one is attached to one of the cushions 22 or 24) to provide therapy to the neck 60.

Figure 7:
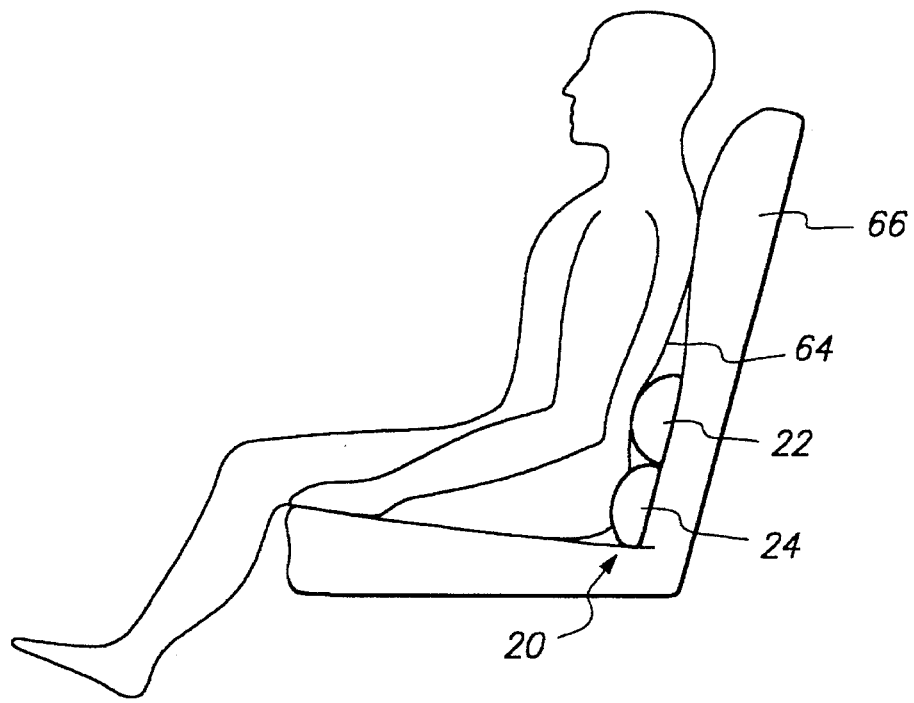

Referring to FIG. 7, the double cushion body support 20 can be used in the open, unzipped position in a seat or chair 66 to provide moderate support to a person's back 64. One of the cushions 22 provides support in the lumbar region of the back 64, while the other cushion 24 provides support to either the region below or above the lumbar region of the back 64. It is believed that the extra support provided to the regions below or above the lumbar region prevents the cushion 22 from creating an uncomfortable strain on the lumbar region. Instead, a comfortable, moderate support is provided. It should be understood that the double cushion body support 20 may be raised or lowered in the seat or chair 66 in order to position the cushions 22 and 24 in the optimum locations on the back 64.

Figure 8:
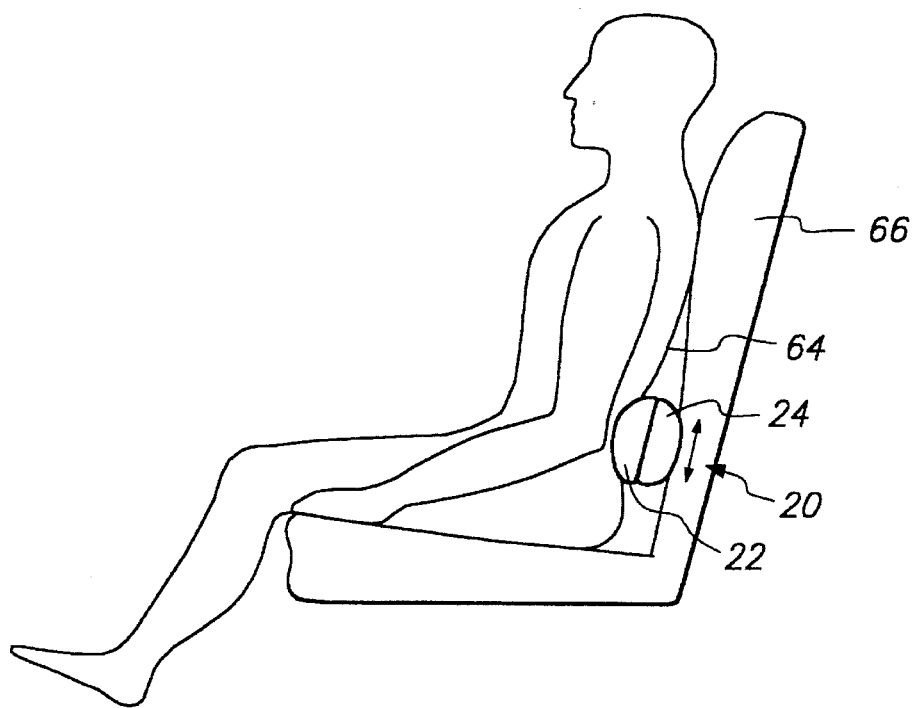

However, if more support is needed in either the lumbar region or the regions below or above the lumbar region of the back 64, the double cushion body support 20 can be used in the closed, zipped position in the seat or chair 66 as shown in FIG. 8. The double cushion body support 20 can be raised or lowered in order to positioned it to provide maximum support to any region of the back 64.

Figure 9:
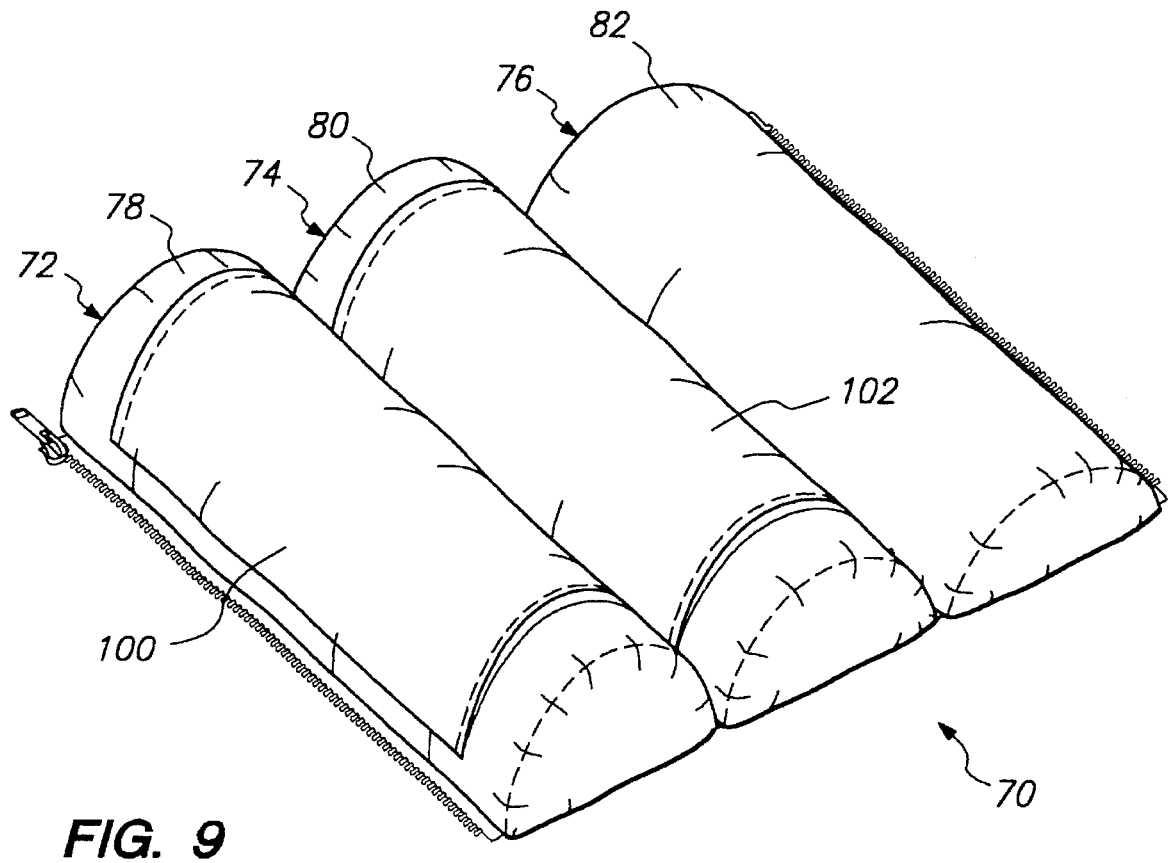
FIG. 9 is a perspective view which illustrates another embodiment of a body support in accordance with the present invention.
Figure 10:
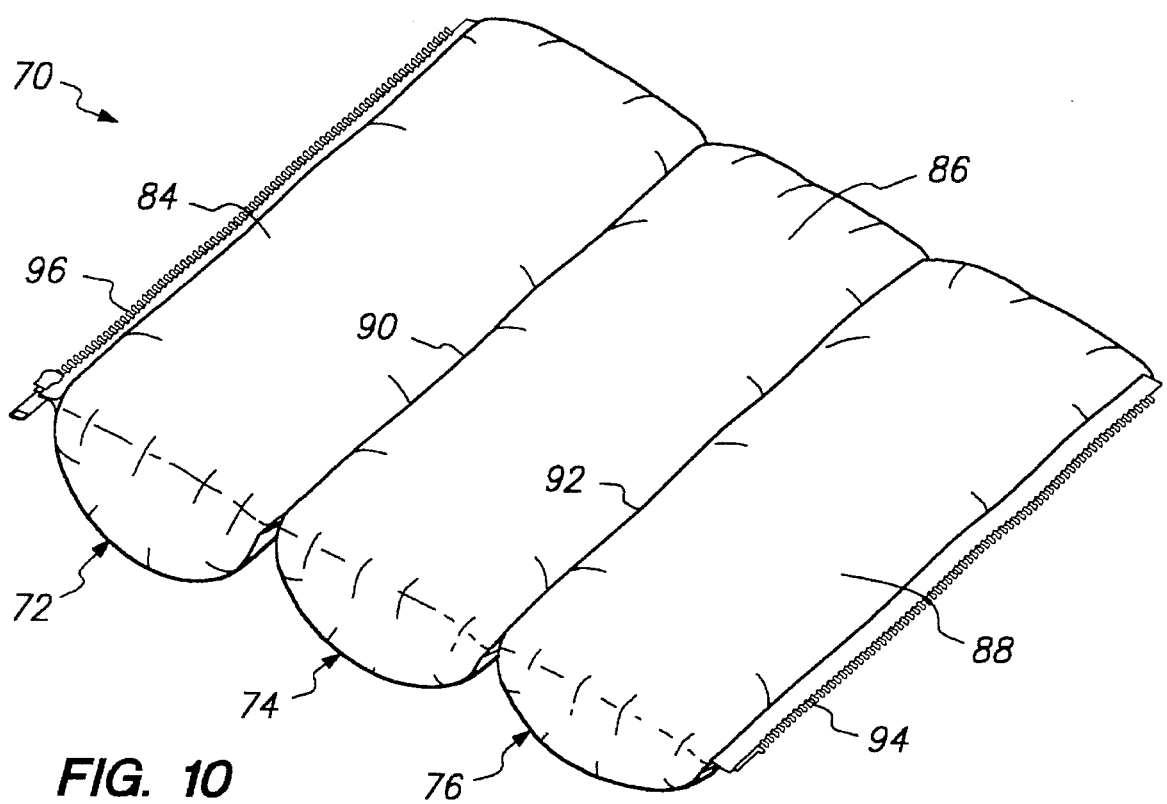
FIG. 10 is a perspective view which illustrates the bottom side of the body support shown in FIG. 9.

FIGS. 9 and 10 illustrate a triple cushion body support 70 in accordance with the present invention. The triple cushion body support 70 includes three substantially semicylindrical shaped cushions 72, 74, and 76 which are hingedly connected together. Each of the cushions 72, 74, and 76 is defined by a semicylindrical top surface 78, 80, and 82, and a substantially rectangular bottom surface 84, 86, and 88, respectively. Each of the bottom surfaces 84, 86, and 88 has two long sides and two short sides.

Unlike the double cushion body support 20 discussed above, the cushions 72, 74, and 76 of the triple cushion body support 70 are not all the same size. Instead, the diameter of the medium cushion 74 is smaller than the diameter of the large cushion 72, and the diameter of the small cushion 76 is smaller than the diameter of the medium cushion 74. In other words, the diameters of the cushions 72, 74, and 76 decreases from one to the next. By way of example, it has been found that a 0.5 inch to 1.5 inch difference between the diameter of one cushion and the neighboring cushion provides comfortable support. By way of example, the large cushion 72 can have a diameter of approximately 6 inches, the medium cushion 74 can have a diameter of approximately 5.25 inches, and the small cushion 76 can have a diameter of approximately 4.5 inches. However, it should be well understood that these are only example diameters and that they may be adjusted without departing from the scope of the present invention.

The materials and stuffing used to construct the triple cushion body support 70 are essentially the same as those used to construct the double cushion body support 20 discussed above. For example, the quantity of stuffing that is contained in the cushions 72, 74, and 76 may be an amount such that the bottom surfaces 84, 86, and 88 are slightly convex in shape, or bulging outward. Furthermore, the cushions 72, 74, and 76 are hingedly connected together along the connection seams 90 and 92 so that the cushions 72, 74, and 76 can be rotated with respect to each other. The manner in which the cushions 72, 74, and 76 are hingedly connected is substantially the same as that discussed above for the double cushion body support 20.

Figure 11:
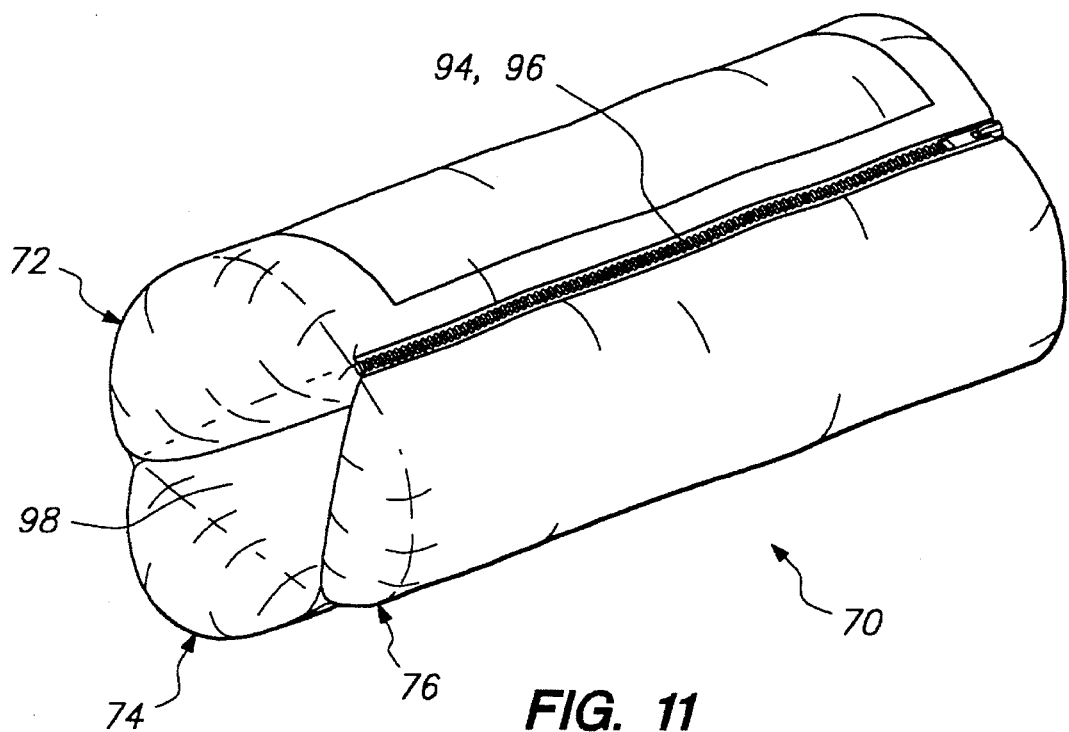
FIG. 11 is a perspective view which illustrates the body support shown in FIG. 9 in the closed position.

The body support 70 can be rotated from an open position, which is shown in FIGS. 9 and 10, to a closed position, which is shown in FIG. 11. In the open position, the long side of the large cushion 72 that is opposite the connection seam 90 is located a maximum distance from the long side of the small cushion 76 that is opposite the connection seam 92.

In the closed position, a zipper section 94 is zipped to a complimentary zipper section 96. Because there are three cushions 72, 74, and 76 instead of only two, there is a gap 98 between the bottom surfaces 84, 86, and 88 when the triple cushion body support 70 is in the closed position. In other words, the bottom surfaces 84, 86, and 88 do not press as tightly against one another as they do in the double cushion body support 20 when in the closed position. Furthermore, the overall size of the triple cushion body support 70 when it is in the closed position is larger than the size of the double cushion body support 20 due to there being three cushions instead of only two. The larger size of the triple cushion body support 70 enables it to provide different degrees of support than the double cushion body support 20.

Although the zipper 94, 96 is the preferred means for securing the triple cushion body support 70 in the closed position, it should again be well understood that other securing and fastening means, such as those discussed above, may be used to secure the triple cushion body support 70 in the closed position.

Similar to the double cushion body support 20, one or more sleeves (or pockets) 100, 102 may be attached to any of the top surfaces 78, 80, or 82 of the cushions 72, 74, or 76 of the triple cushion body support 70 in order to receive and secure a hot or cold pack. In other words, a sleeve is an optional feature and may be attached to one or more of the cushions 72, 74, or 76. Furthermore, one or more of the cushions 72, 74, and 76 may be partially or completely filled with bead-like objects rather than pure polyester fiber. Preferably, such bead-like objects, if they are used, will be contained in either the large cushion 72 or the medium cushion 74.

Figure 12:
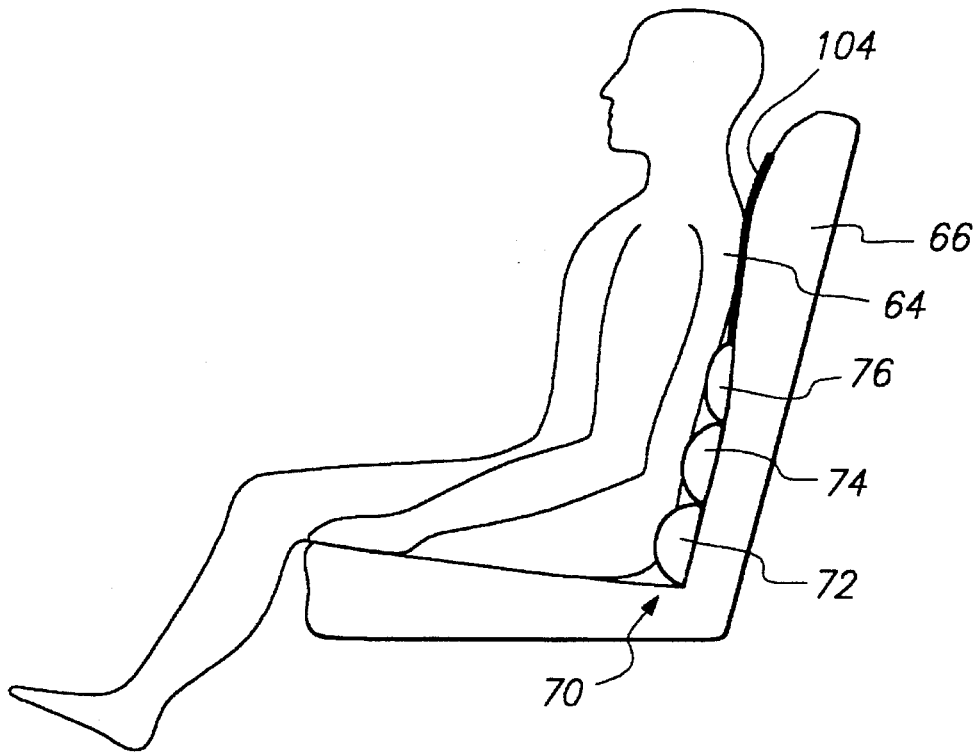
FIGS. 12–13 are side views which illustrate use of the body support shown in FIG. 9.

Referring to FIG. 12, the triple cushion body support 70 can be used in the open, unzipped position in a seat or chair 66 to provide moderate support to a person's back 64. The large cushion 72 is normally positioned near the lower region of the back 64, and the small cushion 76 is normally positioned near the shoulder blade area. Thus, the medium cushion 74 provides support to the lumbar region of the back 64, while the large cushion 72 provides support to the region just below the lumbar region of the back 64. The diameter of the cushions 72, 74, and 76 gets smaller at the higher portions of the back because less support is needed at the shoulder blade area and more support is needed at the lower back. It is believed that the extra support provided by the cushions 72 and 76 permits the medium cushion 74 to provide a very comfortable, moderate support to the lumbar region.

An optional strap 104 may be used to hang the triple cushion body support 70 from the back of the seat or chair 66. The strap 104, for example, may be an elongate piece of material that is attached to the triple cushion body support 70 by way of snaps or VELCRO brand hook and loop type fastening material. The strap 104 can be used to adjust the vertical positioning of the triple cushion body support 70 with respect to the seat or chair 66 and the back 64 in order to give optimum support.

Figure 13:
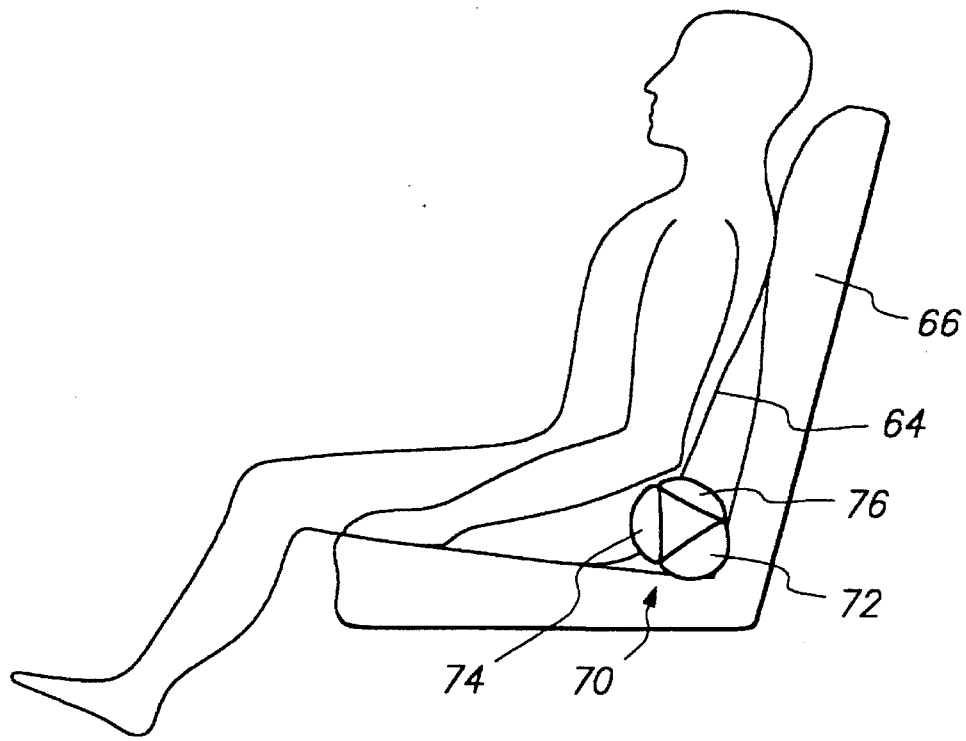

If additional support is needed in either the lumbar region or the regions below or above the lumbar region of the back 64, the triple cushion body support 70 can be used in the closed, zipped position in the seat or chair 66 as shown in FIG. 13. The triple cushion body support 70 can be rotated so that any one of the cushions 72, 74, or 76 makes contact with the back 64. Each of the cushions 72, 74, and 76 will provide a different degree of support to the back 64 because each one has a different diameter. This gives a person flexibility in choosing the desired amount of support. Furthermore, the vertical positioning of the triple cushion body support 70 can be adjusted to provide support to any region of the back 64.

It should be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. A body support, comprising:

a first resilient cushion having a substantially semicylindrical shape defined by a semicylindrical top surface, two substantially semicircular end surfaces, and a substantially rectangular bottom surface having first and second long sides and two short sides, the first cushion containing a first quantity of stuffing such that the substantially rectangular bottom surface of the first cushion has a convex shape;

a second resilient cushion having a substantially semicylindrical shape defined by a semicylindrical top surface, two substantially semicircular end surfaces, and a substantially rectangular bottom surface having first and second long sides and two short sides, the second cushion having a diameter that is approximately equal to a diameter of the first cushion and containing a second quantity of stuffing such that the substantially rectangular bottom surface of the second cushion has a convex shape, the first long side of the second cushion being hingedly connected to the second long side of the first cushion so that the first and second cushions can be rotated with respect to each other from an open position to a closed position in which the substantially rectangular bottom surface of the first cushion is in contact with the substantially rectangular bottom surface of the second cushion; and a zipper having a first zipper section connected along substantially an entire length of the first long side of the first cushion and a second zipper section connected along substantially an entire length of the second long side of the second cushion so that the first and second zipper sections can be zipped together to sqeeze the convex shaped substantially rectangular bottom surfaces of the first and second cushions together in order to increase firmness of the first and second cushions when they are secured in the closed position.

2. A body support as recited in claim 1, wherein one of the cushions is at least partially filled with a multiplicity of bead-like objects.

3. A body support as recited in claim 1, further comprising:

a section of material attached to the semicylindrical top surface of one of the cushions for receiving a hot/cold pack.

4. A method of providing support to a person's neck, comprising the steps of:

securing a body support in a closed position; and positioning the body support in contact with a back portion of the neck;

the body support including:

a first resilient cushion having a substantially semicylindrical shape defined by a semicylindrical top surface, two substantially semicircular end surfaces, and a substantially rectangular bottom surface having first and second long sides and two short sides, the first cushion containing a first quantity of stuffing such that the substantially rectangular bottom surface of the first cushion has a convex shape;

a second resilient cushion having a substantially semicylindrical shape defined by a semicylindrical top surface, two substantially semicircular end surfaces, and a substantially rectangular bottom surface having first and second long sides and two short sides, the second cushion having a diameter that is approximately equal to a diameter of the first cushion and containing a second quantity of stuffing such that the substantially rectangular bottom surface of the second cushion has a convex shape, the first long side of the second cushion being hingedly connected to the second long side of the first cushion so that the first and second cushions can be rotated with respect to each other from an open position to the closed position in which the substantially rectangular bottom surface of the first cushion is in contact with the substantially rectangular bottom surface of the second cushion; and a zipper having a first zipper section connected along substantially an entire length of the first long side of the first cushion and a second zipper section connected along substantially an entire length of the second long side of the second cushion so that the first and second zipper sections can be zipped together to squeeze the convex shaped substantially rectangular bottom surfaces of the first and second cushions together in order to increase firmness of the first and second cushions when they are secured in the closed position.

5. A method as recited in claim 4, wherein one of the cushions is at least partially filled with a multiplicity of bead-like objects.

6. A method as recited in claim 4, wherein the body support further comprises:

a section of material attached to semicylindrical top surface of one of the cushions for receiving a hot/cold pack.

* * * * *